United States Patent [19]

Girgis et al.

[11] 4,290,774

[45] Sep. 22, 1981

[54] PURIFICATION OF LIPOPROTEIN CHOLESTEROL FOR USE AS A CHOLESTEROL REFERENCE MATERIAL

[75] Inventors: Makram M. Girgis, Bradley; David E. Jackson, Bourbonnais; Frank J. Mannuzza, Peotone, all of Ill.

[73] Assignee: Miles Laboratories, Inc., Elkhart, Ind.

[21] Appl. No.: 110,228

[22] Filed: Jan. 7, 1980

[51] Int. Cl.³ .................... G01N 33/68; G01N 33/92; G01N 33/96
[52] U.S. Cl. .................. 23/230 B; 252/408; 260/112 B
[58] Field of Search ............... 23/230 B; 252/408; 260/112 B

[56] References Cited

U.S. PATENT DOCUMENTS 4,096,136 6/1978 Ayers ............................. 260/112 B
4,110,077 8/1978 Klein ........................... 260/112 B X

OTHER PUBLICATIONS

W. Stephan et al., Z. Klin. Chem. Klin. Biochem., 6(3), 186–190 (1968).
W. Werner, J. Chromatog, 25(1), 63–70 (1966).
Chemical Abstracts, 69:17412h (1968).

*Primary Examiner*—Sidney Marantz
*Attorney, Agent, or Firm*—James D. McNeil

[57] ABSTRACT

A method for the purification of lipoprotein cholesterol. The method involves the steps of adsorbing lipoprotein material on a silica adsorbant, eluting the adsorbed lipoprotein with water at a pH of about 10 to 11.5, adjusting the salt concentration to about less than 0.05M, heating the lipoprotein to about 50° to 100° C. for a period of about 5 minutes to 24 hours, adding an alkaline carbonate and alkaline earth salt to form a precipitate and removing the precipitate, adjusting the pH from about 6.5 to 9.0 and recovering purified lipoprotein cholesterol. Also a method for using the cholesterol as a cholesterol reference material.

11 Claims, No Drawings

PURIFICATION OF LIPOPROTEIN CHOLESTEROL FOR USE AS A CHOLESTEROL REFERENCE MATERIAL

BACKGROUND OF THE INVENTION AND PRIOR ART

This invention relates to the purification of lipoproteins to produce a material high in cholesterol content and to the use of such high-cholesterol material as a cholesterol reference standard for determining the cholesterol content of a body fluid.

Determination of serum cholesterol levels is of importance because elevated levels may be useful in the diagnosis of certain maladies. For example, determination of serum cholesterol is used to screen for coronary artery diseases, diabetes mellitus, nephrosis, hepatic and thyroid diseases and metabolic disorders caused by endocrine disturbances.

Clinical chemistry procedures have been developed to enable the determination of cholesterol levels in serum. These procedures generally involve the use of cholesterol reference standards which include human serum and organic salts as components. U.S. Pat. No. 4,045,176 describes the preparation of a cholesterol control standard by adding either higher density human lipoproteins or isolated non-primate lipoproteins (e.g., bovine) to human serum.

U.S. Pat. No. 3,764,556 describes a method for preparing a lipid control sample by isolating a lipid-rich fraction of human plasma and adding equine, bovine or human serum.

U.S. Pat. No. 3,260,648 describes a composition for cholesterol determination which is lyophilized human blood plasma containing an organic solubilizing agent.

Because control standards have been thought to be more reliable if the physical and physiological make-up of the control closely parallels that of the substance to be tested, heretofore cholesterol reference materials have been based on the use of human serum or plasma which have been "adjusted" with organic salts, solubilizing agents or equine, bovine or human serum, as described in the above patents.

Such procedures involving the use of human serum or plasma suffer several disadvantages. First, the presence of human serum or plasma involves a danger to the user due to the possibility of hepatitus virus being present in the serum. Second, the presence of human serum or plasma increases the costs of such a cholesterol control standard.

There is thus a need for a cholesterol reference material that is not used in conjunction with human serum or plasma. The lipoprotein cholesterol of the present invention is suitable for use as a cholesterol reference material in determining the cholesterol content of human serum or plasma, without the presence of human serum or plasma.

Various methods have been used in the art to purify lipoproteins. The most widely used method is ultracentrifugation wherein the lipoprotein classes are separated from the bulk of plasma proteins and from each other by differences in density.

Another purification method involves precipitation and extraction. For example, U.S. Pat. No. 4,104,286 describes isolation of cholesterol from whole egg and dried egg yolk. The patentee describes extraction with ethanol, saponification in aqueous alkali hydroxide and concentration and purification with a hydrocarbon solvent in methanol. Other precipitation methods involve the use of sulfated polysaccharides combined with an alkaline earth. These reagents are relatively specific for lipoprotein precipitation.

A third method involves the adsorption of lipoproteins on inorganic matrices. In contrast to the ultracentrifugation and precipitation and extraction methods where the lipoproteins are purified and recovered, adsorption methods are generally used to remove lipoproteins from serum or plasma; the lipoprotein is then discarded as an impurity. U.S. Pat. No. 4,081,431 describes blood separation wherein a Factor VIII-enriched protein is obtained by removing the lipoprotein-containing Factors II, VII, IX and X as impurities by treatment with silica as a solid adsorbant.

The major stumbling block in using adsorption technology for purification of lipoprotein complexes is the difficulty of recovering the lipoprotein.

The most relevant prior art located appears to be an article in *Zeit. Klin. Chem.* 6 (3) 186–190 (May 1968).

The authors W. Stephan and L. Roka, describe the removal of $\alpha_1$, $\alpha_2$ and $\beta$-lipoproteins from human sera. The method involves adsorbing human sera on colloidal silicic acid. The adsorbed proteins are then centrifuged and frozen, thawed and extracted by the use of a high salt concentration at a pH of 9. According to the authors, recovery of the maximum amount of adsorbed protein occurs at a pH of 9.0 and a salt concentration of 12 percent NaCl weight/volume. The authors disclose that the recovery of the adsorbed protein decreases drastically if the salt concentration varies from a concentration of 12 percent. (This is equivalent to a salt concentration of approximately 2.0 M).

None of the prior art patents, or the article discussed above teaches or suggests the improved results obtained by eluting an adsorbed lipoprotein complex at a pH of 10 to 11.5, adjusting the salt concentration to about less than 0.05 M, heating the eluted lipoprotein, adding an alkaline carbonate and alkaline earth salt, and adjusting the pH from about 6.5 to 9.0. None of the prior art referred to suggests the use of a cholesterol reference material produced as described from plasma or serum which is not used in conjunction with organic salts, solubilizing agents or human plasma or serum.

SUMMARY OF THE INVENTION

The present invention is directed to an improved method for purifying lipoproteins to produce a material high in cholesterol content and to the use of the lipoprotein as a cholesterol reference material. The method involves the steps of adsorbing a lipoprotein, which can be bovine, horse, sheep, pig or human, onto a silica adsorbant; separating the adsorbed lipoprotein from any excess solution; freezing and thawing the adsorbed lipoprotein; eluting the adsorbed lipoprotein at a pH of from 10 to 11.5; concentrating the lipoprotein to a desired concentration; adjusting the pH from about 7.0 to 10.0; adjusting the salt concentration to about less than 0.05 M; heating to about 50° to 100° C. for a period from 5 minutes to 24 hours; adding an alkaline carbonate and alkaline earth salt to form a precipitate and removing the precipitate, adjusting the pH from about 6.5 to 9.0 and recovering purified cholesterol. The purified cholesterol can be used as a cholesterol reference material.

DETAILED DESCRIPTION OF THE INVENTION

The starting material for use in the claimed process can be any plasma or serum fraction that contains cholesterol. Suitable starting materials are obtained from mammalian sources and include bovine, horse, sheep, pig or human plasma, serum, or fraction thereof that contains cholesterol such as fibrinogen-poor plasma, ie., a by-product of fibrinogen preparation such as Cohn Fraction I supernatant, an ammonium sulfate supernatant rich in lipoprotein, ie., a 30 percent $(NH_4)_2SO_4$ supernatant, etc.

If the starting material is a lipoprotein-containing serum, the salt concentration is increased by the addition of a soluble salt, eg., sodium citrate, to a final ionic strength of from about 0.25 to 1.0. Other suitable salts include sodium chloride, sodium phosphate, potassium phosphate, ammonium sulfate and sodium sulfate. Increase of the salt concentration of serum to the level referred to above has been found to increase the amount of lipoprotein adsorbed per unit of siliceous material added. Bovine or human plasma is normally collected by a method which includes addition of citrate as an anti-coagulant and it has been found that normally it is not necessary to increase the salt concentration.

The lipoprotein-containing starting material is maintained at a temperature of from 0° to 50° C., preferably from 15° to 25° C. The pH is adjusted to a range of from 5.5 to 9.0; preferably from 7.0 to 8.0.

Silica adsorbant, in the form of microfine silica particles, commercially available under the trade designation Cabosil, from Cabot Corporation, 125 High St., Boston, Mass. 02110, is added to the starting material in quantities of from 1 to 50 gm per liter; preferably from 10 to 20 gm per liter.

The silica-lipoprotein-containing starting mixture is then mixed for a period of time of from five minutes to six hours; preferably from 3 to 4 hours. The silica particles preferentially absorb the lipoproteins present and form a silica/lipoprotein complex having a gel-like appearance. Excess solution is removed from the gel by conventional liquid/solid separation techniques, eg., centrifugation.

The silica/lipoprotein gel is cooled at about −20° C. for a period of time sufficient to allow all of the gel to become frozen. Depending upon the container configuration and sample volume, from about 1 to 30 days is sufficient. The gel is allowed to thaw and the liquid that is expressed from the complex is discarded.

The gel is suspended in dilute salt solution, eg., 0.15 M sodium chloride, sodium acetate or sodium phosphate (approximately a saline volume equal to twice the weight of the paste) at a pH of about 7.0 and allowed to settle. The supernatant is removed from the settled gel and the washing procedure is repeated two or three times with dilute salt solution. The use of dilute salt solution ensures the solubility and removal of undesired proteins, e.g., euglobulins which are present in the interparticle space of the gel.

The washed gel is eluted by suspending it in 2 to 3 times its volume of distilled or deionized water at a pH adjusted to a range of from 10.0 to 11.5; preferably from 10.4 to 10.6. The mixture is stirred for about 3 to 4 hours and the pH maintained within the desired range. The mixture is then allowed to settle.

The supernatant is siphoned off and set aside. Elution of the gel, stirring and siphoning is repeated two more times and the supernatant portions combined.

The combined supernatant fractions are concentrated by conventional methods, eg., precipitation by addition of salts and neutral polymers; adsorption/desorption methods; evaporation or preferably by ultrafiltration. The supernatant is concentrated to any desired cholesterol concentration of from 50 to 3000 mg/dl preferably about 1000 to 2000 mg/dl.

The cholesterol concentration can be determined by conventional enzymatic or non-enzymatic methods. For a description of enzymatic methods see *Ann. Clin. Biochem.* 10:79–84 (1973) and *Clin. Chem.* 19:1350–1356 (1973). For a description of a non-enzymatic method involving the use of ferric acetate, uranium acetate and sulfuric acid-ferrous sulfate reagents, see *Annal. Chem.* 42:1432 (1970).

The lipoprotein material is treated by conventional methods to remove substantially all salt present, eg., ion exchange; gel permeation; dialysis or preferably dialysis by ultrafiltration. The final salt concentration, calculated as chloride is less than about 0.05 M; preferably 0 to 0.005 M. The pH is adjusted to a range of from 7.0 to 10.0; preferably about 8.5. It has been found that the salt concentration is critical; if the heating step is conducted in the presence of significant amounts of salt, an undesirable amount of denaturation of the lipoprotein cholesterol occurs.

The solution is heated to a temperature in the range of from 50° to 100° C. for a period of time of from 5 minutes to 24 hours; preferably to 80° C. for about 4 to 8 hours. The heating step eliminates deleterious bacteria and unwanted enzymes and increases the storage stability of the lipoprotein cholesterol.

Following the heating step, an alkaline carbonate and alkaline earth salt are added to the cholesterol suspension.

This addition markedly improves the clarity of the lipoprotein cholesterol obtained. From about 0.1 to 1.0 M $Na_2CO_3$ and from about 1 mM to 100 mM $MnCl_2$ are effective. About 0.5 M $Na_2CO_3$ and from 5 to 10 mM $MnCl_2$ are preferred. The alkaline carbonate salt and alkaline earth salt produce a precipitate of denatured proteins which is separated from the cholesterol by centrifugation. The cholesterol is adjusted to a pH in the range of from 6.5 to 10.0; preferably 9.0. Preferably the cholesterol is made substantially salt-free by conventional methods, e.g., ion-exchange, gel filtration dialysis by ultrafiltration.

The solution is then adjusted to a pH in the range of from 6.5 to 9.0 and heated as described previously. Alternately the lipoprotein can be sterile-filtered by filtration through membrane filters.

EXAMPLE 1

Pooled normal bovine having serum was collected and brought to a temperature of about 20°–25° C. The ionic strength of the serum was adjusted to a range of from 0.5 to 1.0 by adding solid sodium citrate to a final concentration of 50 mM. The pH of the serum was adjusted to a pH of about 7.0 by addition of 1 N HCl or 1 N NaOH, as required. Silica adsorbant, in the form of microfine silica was added, in an amount of 10 gm per liter of serum, and the silica-lipoprotein complex formed was mixed for about 4 hours.

The complex was centrifuged and frozen at −20° C. After a period of one week, the frozen complex was thawed by allowing it to sit at room temperature; thawing produced a paste-like material. Normal saline (0.15 M NaCl) was added to the paste; the volume added was equal to twice the weight of the paste. The mixture was stirred for about 15 minutes; the solids present were allowed to settle by gravity and the resulting clear supernatant siphoned off. The supernatant contained contaminants trapped in the paste and was discarded. The addition of saline and removal and discarding of the supernatant fraction was repeated two to three times.

Deionized water was added to the paste; the volume added was equal to twice the weight of the paste. The suspension was mixed and the pH adjusted to 10.4 by the addition of 1 N NaOH. Mixing was continued for about 2 to 3 hours; the pH was maintained at 10.4 by the addition of 1 N NaOH. After mixing was stopped, the solids present were allowed to settle and the clear supernatant, containing the desired lipoprotein fraction, was set aside. The steps of adding deionized water, mixing pH adjustment and removal of the lipoprotein-containing supernatant fraction was repeated two times. The supernatant proteins were combined and held at 5° C. The combined supernatant fraction was centrifuged to remove any residual silica present and concentrated by ultrafiltration; a cholesterol value of about 1000 mg/dl was obtained.

The concentrated lipoprotein fraction was then dialyzed by ultrafiltration using about three replacement volumes of deionized water until the salt concentration measured as NaCl was reduced to approximately 0.002 M.

The pH of the lipoprotein fraction was adjusted to about 8.0 by the addition of 1 N HCl and the lipoprotein fraction heated to 80° C. and held at this temperature for a period of 4 hours.

The lipoprotein fraction was cooled to room temperature. To obtain additional clarification of the lipoprotein fraction, 2 M $Na_2CO_3$ was added to a final concentration of 0.24 M and 0.1 M $MnCl_2$ was added to a final concentration of 6 mM. A precipitate containing denatured proteins was removed by centrifugation and discarded as a contaminant. The lipoprotein-containing solution was adjusted to a pH of 9.0 by addition of 1 N HCl. The solution was then concentrated by ultrafiltration; a cholesterol value of about 1500 mg/dl was obtained. The concentrated lipoprotein cholesterol fraction was then dialyzed by ultrafiltration using six replacement volumes of deionized water to remove any salt present. The final salt concentration measured as NaCl was determined to be less than 0.05 M. The lipoprotein cholesterol material was then heated to 80° C. and held at this temperature for a period of 8 hours.

The purified lipoprotein cholesterol at a cholesterol value of 1300 mg/dl was analyzed and determined to have the following characteristics: optical density at 710 nm of less than 0.15; easily sterile filtered, bacteria less than 10 organisms/ml; clarity is unaffected by heating to as high as 100° C. for at least 1 hour; clarity and cholesterol value are stable for at least 2 years at +5° C.; clarity is unaffected by multiple freeze-thaw cycles; the lipoprotein electrophoretic profile on cellulose acetate or acrylamide is not characteristic of a bovine lipoprotein profile.

The chemical analysis of the lipoprotein cholesterol indicated the following:

Total protein less than 4.0 gm/dl
Inorganic phosphorus less than 1 mg/dl
Calcium less than 2 mg/dl
Glucose less than 20 mg/dl
Blood urea nitrogen less than 2 mg/dl
Total bilirubin less than 0.2 mg/dl
Sodium less than 25 mg/l
Potassium less than 1 mg/l
Chloride less than 10 mg/l
Creatinine less than 0.2 mg/dl
Uric acid less than 0.2 mg/dl
Lactate dehydrogenase less than 10 M$\mu$/l
Creatinine phosphokinase less than 40 M$\mu$/l
$\alpha$-glutamyltransferase less than 100 M$\mu$/l
Serum glutamic oxalacetic transaminase less than 20 M$\mu$/l
Glutamic pyruvate transaminase less than 30 M$\mu$/l Because the bovine lipoprotein cholesterol of the present invention has a cholesterol ester:free cholesterol ratio (approximately 70:30) essentially the same as found in human serum, the cholesterol material can be used as a cholesterol reference material, without being added to human serum or human plasma.

The purified lipoprotein cholesterol was used as a cholesterol reference standard as follows. A series of control standards, containing varying concentrations of cholesterol, was prepared by diluting the lipoprotein material with distilled or deionized water to a range of 75–100 mg/dl; 150–200 mg/dl; and 450–500 mg/dl. These levels correspond respectively with "low", "normal" and "elevated" levels of cholesterol in humans.

Samples of the bovine lipoprotein cholesterol prepared by the method described above were assayed and assigned the following assay values:

Sample 1: 100 mg/dl cholesterol
Sample 2: 250 mg/dl cholesterol
Sample 3: 460 mg/dl cholesterol by an enzymatic cholesterol assay method [See Allain, et. al. *Clinical Chemistry* 20:470 (1974)], using a kit commercially available from E. I. duPont de Nemours, Wilmington, Del. sold under the trade designation DuPont ACA.

In order to determine whether the purified bovine lipoprotein cholesterol would function effectively as a cholesterol reference material, the samples having the above assay values were sent to independent clinical testing laboratories for incorporation in their routine cholesterol determinations. A total of seven independent laboratories incorporated three 10 ml sample solutions of the high, normal and elevated levels in their routine cholesterol determination procedures and reported within-day and day-to-day precision and accuracy. The following mean values were obtained.

| | Lipoprotein Cholesterol Solutions | | |
|---|---|---|---|
| | 100 mg/dl | 250 mg/dl | 460 mg/dl |
| Lab #1 | 103.5 | 261.8 | 439.3 |
| Lab #2 | 99.6 | 250.6 | 450.4 |
| Lab #3 | 111.0 | 270.7 | 489.8 |
| Lab #4 | 101.1 | 291.7 | 503.4 |
| Lab #5 | 81.7 | 222.5 | 400.3 |
| Lab #6 | 117.3 | 287.3 | 512.5 |
| Lab #7 | 103.5 | 261.8 | 494.1 |

In terms of the study conducted, accuracy refers to the extent to which assigned assay values agree with or approach the values obtained by other methods; precision refers to the closeness with which repeated analyses agree.

Standard statistical methods of analysis were applied to all of the data from the testing laboratories. (For a complete discussion of the use of such control materials and statistical methods of analysis, see *Clinical Chemistry: Principles and Technics,* Second edition, pp 302–321).

Based on this study, in terms of accuracy and precision, the lipoprotein cholesterol solutions of the present invention are effective as a cholesterol reference material in the determination of the cholesterol content of test samples. The solutions provide a means for both estimating precision and for detecting systematic analytical deviations.

For preparation of liquid control samples, which are amenable to autoclaving treatment, the lipoprotein cholesterol material is diluted to the "low", "normal" and "elevated" range by adding distilled or deionized water. The samples are then sterilized by steam autoclaving at about 120° C. at a pressure of about 15 psi.

For preparation of liquid control samples by sterile filtering, the lipoprotein cholesterol material is diluted by adding distilled or deionized water; dilute salt solutions such as normal saline or protein solutions, e.g., bovine albumin or non-primate animal serum.

In addition, liquid control samples can be prepared by adding a bactericide, e.g., sodium azide or mercury salts.

For preparation of a lyophilized purified lipoprotein cholesterol control standard, the lipoprotein cholesterol material is diluted with a protein-containing diluent such as bovine albumin or non-primate serum. Optionally, bactericides such as sodium azide, mercury salts or antibiotics can be added.

What is claimed is:

1. In a method for purifying lipoprotein cholesterol which involves the steps of adsorbing a solution of a lipoprotein-containing substance onto a silica adsorbant, separating the adsorbed lipoprotein from any excess solution present, freezing and thawing the adsorbed lipoprotein, eluting the adsorbed lipoprotein, concentrating the lipoprotein to a desired concentration and recovering purified lipoprotein cholesterol therefrom, the improvement comprising the steps of eluting the adsorbed lipoprotein at a pH from about 10 to 11.5, adjusting the salt concentration to about less than 0.05 M, heating the eluted lipoprotein to a temperature of from about 50° to 100° C. for a period of time sufficient to increase the storage stability of the purified lipoprotein cholesterol, adding an alkaline carbonate and an alkaline earth salt; adjusting the pH from about 6.5 to 9.0; and recovering therefrom said lipoprotein cholesterol.

2. A method as claimed in claim 1 wherein the lipoprotein-containing substance is bovine lipoprotein.

3. A method as claimed in claim 2 wherein the pH is maintained from about 10.4 to 10.6 during the eluting step.

4. A method as claimed in claim 2 wherein the temperature is maintained at about 80° C. for a period of about 8 hours.

5. A method as claimed in claim 2 which additionally includes the steps of diluting the cholesterol with a protein-containing diluent and lyophilizing the cholesterol.

6. A method as claimed in claim 2 wherein from 0.1 to 1.0 M alkaline carbonate and from 1 mM to 100 mM alkaline earth salt are added.

7. A method for purifying lipoprotein cholesterol which comprises the steps of:

(a) adsorbing a solution of lipoprotein-containing substance onto a silica adsorbant;
(b) separating the adsorbed lipoprotein from any excess solution present;
(c) freezing and thawing the adsorbed lipoprotein;
(d) eluting the adsorbed lipoprotein at a pH of from about 10 to 11.5;
(e) concentrating the lipoprotein obtained from step (d) to a desired concentration of cholesterol;
(f) adjusting the pH of the lipoprotein from about 7.0 to 10.0;
(g) adjusting the salt concentration to about less than 0.05 M;
(h) heating the lipoprotein to a temperature of from about 50° to 100° C. for a period of about 5 minutes to 24 hours;
(i) adding an alkaline carbonate and an alkaline earth salt;
(j) adjusting the pH of the lipoprotein from about 6.5 to 9.0; and
(k) recovering therefrom purified lipoprotein cholesterol.

8. A method as claimed in claim 7 wherein the lipoprotein-containing substance is bovine lipoprotein.

9. A method as claimed in claim 7 which additionally includes the steps of diluting the cholesterol with a protein-containing diluent and lyophilizing the cholesterol.

10. A purified lipoprotein cholesterol prepared by the steps of:

(a) adsorbing a solution of lipoprotein-containing substance onto a silica adsorbant;
(b) separating the adsorbed lipoprotein from any excess solution present;
(c) freezing and thawing the adsorbed lipoprotein;
(d) eluting the adsorbed lipoprotein at a pH of from about 10 to 11.5;
(e) concentrating the lipoprotein obtained from step (d) to a desired concentration of cholesterol;
(f) adjusting the pH of the cholesterol from about 7.0 to 10.0;
(g) adjusting the salt concentration to about less than 0.05 M;
(h) heating the cholesterol to a temperature of from about 50° to 100° C. for a period of about 5 minutes to 24 hours;
(i) adding an alkaline carbonate and an alkaline earth salt;
(j) adjusting the pH of the cholesterol from about 6.5 to 9.0; and
(k) recovering therefrom purified lipoprotein cholesterol.

11. A method of determining the cholesterol content of a test sample which includes the step of using as a cholesterol reference material a composition consisting essentially of purified lipoprotein cholesterol prepared by the steps of:

(a) adsorbing a solution of lipoprotein-containing substance onto a silica adsorbant;
(b) separating the adsorbed lipoprotein from any excess solution present;
(c) freezing and thawing the adsorbed lipoprotein;
(d) eluting the adsorbed lipoprotein at a pH of from about 10 to 11.5;
(e) concentrating the lipoprotein obtained from step (d) to a desired concentration of cholesterol;
(f) adjusting the pH of the cholesterol from about 7.0 to 10.0;

(g) adjusting the salt concentration to about less than 0.05 M;

(h) heating the cholesterol to a temperature of from about 50° to 100° C. for a period of about 5 minutes to 24 hours;

(i) adding an alkaline carbonate and an alkaline earth salt to form a precipitate and removing the precipitate;

(j) adjusting the pH of the cholesterol from about 6.5 to 9.0; and (k) recovering therefrom purified lipoprotein cholesterol.

* * * * *

UNITED STATES PATENT AND TRADEMARK OFFICE
CERTIFICATE OF CORRECTION

PATENT NO. : 4,290,774
DATED : September 22, 1981
INVENTOR(S) : Makram Melek Girgis, et al It is certified that error appears in the above-identified patent and that said Letters Patent are hereby corrected as shown below:

Claim 10, subparagraph (i), insert after the word "salt", --to form a precipitate and removing the precipitate--.

Claim 11, subparagraph (i), delete "to form a precipitate and removing the precipitate".

Signed and Sealed this

Fifth Day of June 1984

[SEAL]

Attest:

GERALD J. MOSSINGHOFF

Attesting Officer

Commissioner of Patents and Trademarks